United States Patent
Yale

(10) Patent No.: US 11,806,645 B1
(45) Date of Patent: Nov. 7, 2023

(54) METHODS OF PRODUCING CBD/THC OILS

(71) Applicant: Cannaceutical Extractions LLC, Cottage Grove, OR (US)

(72) Inventor: Matt Yale, Cottage Grove, OR (US)

(73) Assignee: Cannaceutical Extractions LLC, Cottage Grove, OR (US)

( * ) Notice: Subject to any disclaimer, the term of this patent is extended or adjusted under 35 U.S.C. 154(b) by 428 days.

(21) Appl. No.: 16/405,008

(22) Filed: May 7, 2019

(51) Int. Cl.
| | |
|---|---|
| *B01D 3/10* | (2006.01) |
| *B01D 3/08* | (2006.01) |
| *B01D 15/38* | (2006.01) |
| *B01D 39/18* | (2006.01) |
| *B01J 8/02* | (2006.01) |
| *B01D 11/02* | (2006.01) |
| *B01J 8/00* | (2006.01) |
| *C07C 39/08* | (2006.01) |
| *C07D 311/80* | (2006.01) |
| *C07C 37/00* | (2006.01) |

(52) U.S. Cl.
CPC .................. *B01D 3/10* (2013.01); *B01D 3/085* (2013.01); *B01D 11/0292* (2013.01); *B01D 15/3804* (2013.01); *B01D 39/18* (2013.01); *B01J 8/006* (2013.01); *B01J 8/02* (2013.01); *B01D 2239/1241* (2013.01); *B01J 2220/4806* (2013.01); *C07C 37/004* (2013.01); *C07C 39/08* (2013.01); *C07D 311/80* (2013.01)

(58) Field of Classification Search
None
See application file for complete search history.

(56) References Cited

U.S. PATENT DOCUMENTS

| | | | |
|---|---|---|---|
| 3,156,614 | A | 11/1964 | MacDonnell |
| 6,365,416 | B1* | 4/2002 | Elsohly et al. ......... G01N 30/12 |
| | | | 436/161 |
| 6,713,048 | B2 | 3/2004 | Peart et al. |
| | | (Continued) | |

FOREIGN PATENT DOCUMENTS

| | | |
|---|---|---|
| AU | 2015280412 A1 | 1/2017 |
| AU | 2018253527 A1 | 11/2018 |
| | (Continued) | |

OTHER PUBLICATIONS

Ichibancrafter, Super-Cooled QWET Wash for Cannabis Extraction Using Dry Ice, 2016, https://extractcrafter.com/2016/07/27/super-cooled-qwet-wash-for-cannabis-extraction-using-dry-ice/ [last visited Jan. 5, 2020]. (Year: 2016).*

(Continued)

*Primary Examiner* — In Suk C Bullock
(74) *Attorney, Agent, or Firm* — Chernoff, Vilhauer, McClung & Stenzel, LLP

(57) ABSTRACT

Methods of producing a CBD/THC oil are disclosed. In some embodiments, the method may include extracting CBD/THC from plant matter using one or more solvents, winterizing the solvent extract, and evaporating the one or more solvents from the winterized extract. The method may additionally include distilling the evaporated extract via a short path distillation apparatus to produce an initial distillate oil, mixing the initial distillate oil with at least one solvent, and running the mixture of initial distillate oil and at least one solvent through a chromatography column to produce an effluent. The method may further include evaporating the at least one solvent from the effluent, distilling the evaporated effluent via a short path distillation apparatus to produce a final distillate oil, and mixing one or more desired terpenes with the final distillate oil.

15 Claims, 1 Drawing Sheet

(56) References Cited

U.S. PATENT DOCUMENTS

| | | | |
|---|---|---|---|
| 8,980,941 | B2 | 3/2015 | Hospodor |
| 9,937,218 | B2* | 4/2018 | Towle ................. A61K 36/185 |
| 2005/0079136 | A1 | 4/2005 | Woolfe et al. |
| 2007/0104741 | A1 | 5/2007 | Murty et al. |
| 2010/0196488 | A1 | 8/2010 | Whittle |
| 2010/0273895 | A1 | 10/2010 | Stinchcomb et al. |
| 2012/0095087 | A1 | 4/2012 | Hyatt |
| 2012/0304990 | A1 | 12/2012 | Todd |
| 2017/0209409 | A1 | 7/2017 | Hartman et al. |

FOREIGN PATENT DOCUMENTS

| | | |
|---|---|---|
| CA | 2952934 A1 | 12/2015 |
| EP | 3160445 A1 | 5/2017 |

OTHER PUBLICATIONS

Ichibancrafter, Winterizing & Polishing BHO Extracts Using Ethanol, 2017, https://extractcrafter.com/2017/12/04/winterizing-polishing-bho-extracts-using-ethanol/ [last retrieved Jan. 5, 2020] [hereinafter Ichibancrafter II]. (Year: 2017).*

Labcompare, 2016, Automating Solvent Removal from Winterized Cannabis Oil Extract, https://www.labcompare.com/10-Featured-Articles/190804-Automating-Solvent-Removal-From-Winterized-Cannabis-Oil-Extract/ [last visited Jan. 3, 2020]. (Year: 2016).*

M. Rice, Using Short-Path Distillation to Extract CBD Oil From Cannabis, 2018, Azo Materials, https://www.azom.com/article.aspx?ArticleID=17026 [last visited Jan. 5, 2020] (Year: 2018).*

Seppic, Solubility Enhancement and Emulsion Formulation, 2018, https://www.seppic.com/emulsifierssolubilizers [last visited Jan. 5, 2020]. (Year: 2018).*

Zamnesia, Beyond Cannabinoids: Flavonoids, Terpenes, and Terpenoids of Cannabis, 2014, https://www.zamnesia.com/blog-beyond-cannabinoids-flavonoids-terpenes-terpenoids-of-cannabis-n301 [last visited Jan. 3, 2020]. (Year: 2014).*

* cited by examiner

METHODS OF PRODUCING CBD/THC OILS

FIELD

This disclosure relates to methods of producing cannabidiol (CBD) and/or tetrahydrocannabinol (THC) oils. More specifically, the disclosed embodiments relate to methods of producing CBD/THC oils for inhalers.

BACKGROUND

Cannabidiol (CBD) and tetrahydrocannabinol (THC) are two primary cannabinoids that occur naturally in the Cannabis sativa plant, which is most commonly known as cannabis. CBD/THC oil is created or produced from the stems, stalks, and/or leaves of the Cannabis sativa plant. Different strains of the Cannabis sativa plant have different amounts of CBD and/or THC compounds. For example, one strain may have high THC and low CBD (e.g., 10-30% THC, trace amounts of CBD), balanced CBD/THC (e.g., 5-15% THC and CBD), or high CBD and low THC (e.g., 5-20% CBD, THC under 5%).

SUMMARY

The present disclosure provides methods of producing a CBD and/or THC (CBD/THC) oil. In some embodiments, the method may include extracting CBD/THC from plant matter using one or more solvents, winterizing the solvent extract, and evaporating the one or more solvents from the winterized extract. The method may additionally include distilling the evaporated extract via a short path distillation apparatus to produce an initial distillate oil, mixing the initial distillate oil with at least one solvent, and running the mixture of initial distillate oil and at least one solvent through a chromatography column to produce an effluent. The method may further include evaporating the at least one solvent from the effluent, distilling the evaporated effluent via a short path distillation apparatus to produce a final distillate oil, and mixing one or more desired terpenes with the final distillate oil.

Features, functions, and advantages may be achieved independently in various embodiments of the present disclosure, or may be combined in yet other embodiments, further details of which can be seen with reference to the following description and drawings.

DESCRIPTION

Figure 1:
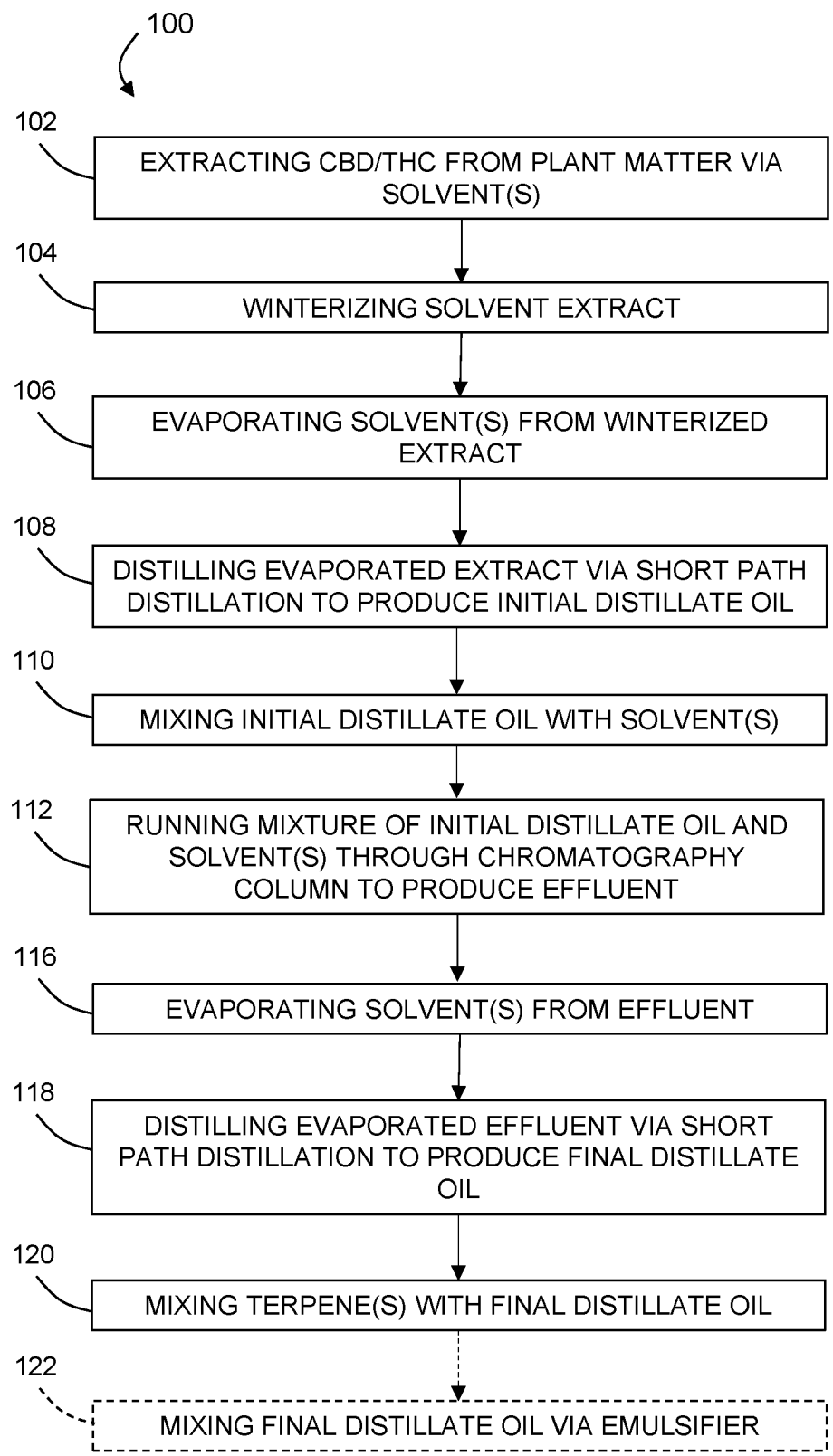
FIG. 1 is a flowchart showing an example of a method of producing a CBD/THC oil.

Various aspects and examples of methods of producing a CBD/THC oil are described below and illustrated in the associated drawings. Unless otherwise specified, methods of producing a CBD/THC oil may contain or be associated with at least one of the structures, components, functionalities, and/or variations described, illustrated, and/or incorporated herein. Furthermore, unless specifically excluded, the process steps, structures, components, functionalities, and/ or variations described, illustrated, and/or incorporated herein in connection with the present teachings may be included in other similar devices and methods, including being interchangeable between disclosed embodiments. The following description of various examples is merely illustrative in nature and is in no way intended to limit the disclosure, its application, or uses. Additionally, the advantages provided by the examples and embodiments described below are illustrative in nature and not all examples and embodiments provide the same advantages or the same degree of advantages.

Examples, Components, and Alternatives

The following sections describe selected aspects of illustrative methods of producing a CBD/THC oil. The examples in these sections are intended for illustration and should not be interpreted as limiting the entire scope of the present disclosure. Each section may include one or more distinct embodiments or examples, and/or contextual or related information, function, and/or structure. Additionally, although the methods are described to produce a CBD/ THC oil, the methods may alternatively, or additionally, produce oil with one or more other cannabinoids.

A. Illustrative Methods of Producing a CBD/THC Oil

This section describes an illustrative method of producing a CBD/THC oil, depicted at 100 in FIG. 1. CBD and/or THC compounds are extracted from plant matter via one or more solvents at step 102. Any suitable solvents may be used to extract the CBD/THC compounds. 95% to 100% ethanol is a preferred solvent for extraction. A propane/n-butane mixture is more preferred. In particular, an about 70% propane and about 30% butane mixture is even more preferred as the solvent for extraction. The solvent(s) may be cooled or chilled below 0° C. prior to being used for extraction. Cooling the solvent(s) to about -40° C. to about -80° C. is preferred, and to about -60° C. is more preferred.

Extracting CBD and/or THC compounds with solvent(s) may be performed using any suitable solvent extraction equipment. Plant matter is generally packed into one or more material columns and the solvent(s) are pushed through the material columns to allow the plant matter to soak in the solvent(s), such as for up to 30 minutes. An inert gas, such as nitrogen at a maximum pressure of 30 psi, may be used to push the solvent(s) into the material columns and/or to push the solvent(s) out of those columns. The columns may be jacketed or sleeved to help maintain the sub-zero temperatures of the solvent(s). The solvent(s) may alternatively, or additionally, be recirculated through the packed plant matter via one or more pumps. The extraction step produces a solvent extract having the CBD and/or THC compounds in the solvent(s). Examples of suitable solvent extraction equipment are available from Open Source Steel in Kelso, Washington (www.opensourcesteel.com) and Precision Extraction Solutions in Troy, Michigan (www.precisionextraction.com).

The solvent extract is then winterized at step 104. One or more solvent(s) are added to the extract to produce a winterizing mixture. A preferred solvent is 95% to 100% ethanol. The solvent(s) are added at any suitable ratios to produce the winterizing mixture. A preferred ratio is 6 parts solvent(s) and 1 part extract. The winterizing mixture is then placed in a cryogenic freezer at about -40° C. to about -80° C. for about 4 to about 8 hours. The chilled winterizing mixture is then filtered to remove unwanted lipids and/or waxes. The mixture may be filtered through two or more filters with decreasing micron ratings to provide a winterized extract. Preferably, the chilled winterizing mixture is run through a first filter having an about 20 micron rating, a second filter having an about 5 to about 7 micron rating, and then a third filter having an about 1 to about 3 micron rating. Paper filters may be used for the filters for ease of use and disposal. However, other nonpaper filters also may be used.

The solvent(s) in the winterized extract is then evaporated at step 106 to at least substantially remove the solvent(s) from the winterized extract to produce an evaporated extract. The winterized extract is heated to about 70° C. to about 90° C. Temperatures higher than 90° C. may evaporate and/or degrade the CBD and/or THC compounds. The evaporated solvent(s) can be recovered and reused for one or more other steps of method 100. Suitable equipment for evaporating the solvent(s) includes a rotary evaporator.

The evaporated extract is then distilled at step 108. Distillation is performed using a short path distillation apparatus, a heating device, and a vacuum pump to reduce boiling points of the compounds contained within the evaporated extract. A suitable short path distillation apparatus is the G2 Short Path Distillation Kit available from Lab Society (www.labsociety.com). In the short path distillation apparatus, the evaporated extract is heated via the heating device to increase the temperature of the evaporated extract. The distillate oil is collected in two or more batches with each of the batches being associated with different temperature ranges of the evaporated extract. The evaporated extract is heated to about 130° C. to about 150° C. and the first batch of distillate oil is collected. The first batch of distillate oil generally will include terpenes, heat-sensitive impurities, triglycerides, solvent residuals, and/or other undesired components.

The evaporated extract is then heated to about 160° C. Once the temperature of the evaporated extract is stable for about 20 minutes, the temperature is increased slowly until about 180° C. Preferably, the temperature setting of the heating device is raised in 10° C. increments every 15 minutes until the evaporated extract is at about 180° C. The second batch of distillate oil is collected between about 160° C. and about 180° C. The second batch is collected when the evaporated extract is about 160° C. and as the temperature of the evaporated extract is being slowly increased. When only a second batch of distillate oil is collected, that distillate oil may be referred to as the "initial distillate oil" or "first pass distillate oil."

Preferably, a third batch of distillate oil is collected during the increase of temperature to about 180° C. One or more characteristics of the distillate oil may change during the temperature increase between about 160° C. and about 180° C. The third batch may be collected when there is change in the characteristic(s). In some embodiments, there is a change in tone and/or color in the distillate oil and the darker tone/darker color distillate oil (e.g., lighter color to redder) is preferably collected in the third batch. The second batch of distillate oil may have a higher purity of CBD and/or THC compounds compared to the third batch of distillate oil. When a third batch is collected, the second and third batches of distillate oil from step 108 are processed separately under steps 112-122. In some embodiments, steps 102-108 may be repeated to produce greater volumes of the second and/or third batches prior to performing steps 112-122. One or both of the second and third batches of distillate oil from step 108 may be referred to as "initial distillate oil" or "first pass distillate oil."

One or more solvents are mixed with the initial distillate oil at step 110. Suitable solvents include non-polar solvents. Pentane and hexane are preferred, while n-heptane is more preferred. Any suitable ratio of solvent and initial distillate oil may be used to create the mixture. A 4:1 weight ratio of solvent to initial distillate oil is preferred.

The solvent and initial distillate oil mixture is then run through at least one chromatography column at step 112 to remove pigments and/or impurities from the initial distillate oil producing an effluent. A suitable chromatography column is made by Chemglass and is available from Thomas Scientific (www.thomassci.com). The chromatography column includes a stationary bed having inert solids, such as silica or silicon dioxide. A stationary bed with activated magnesium silicate is preferred, which is available as Mag-Sil-PR from Lab Society (www.labsociety.com). The activated magnesium silicate binds to polar, water soluble compounds and also allows for separation of fats/lipids due to its particles size. Even more preferred is a stationary bed having 350 ml of silica, 350 ml of carbon, 250 ml of activated magnesium silicate, and 250 ml of hydrated magnesium acid silicate. Hydrated magnesium acid silicate is available as Magnesol® through the Dallas Group of America, Inc. in Whitehouse, New Jersey.

The solvent(s) is evaporated from the effluent at step 116 to produce an evaporated effluent. The effluent is heated to about 70° C. to about 90° C. Temperatures higher than 90° C. may evaporate and/or degrade the CBD and/or THC compounds. The evaporated solvent(s) can be recovered and reused for one or more other steps of method 100. Suitable equipment for evaporating the solvent(s) includes a rotary evaporator.

The evaporated effluent is then distilled at step 118. Distillation is performed using a short path distillation apparatus, a heating device, and a vacuum pump to reduce boiling points of the compounds contained within the evaporated effluent. The short path distillation apparatus for step 118 may be the same or different from the apparatus used for step 108. In the short path distillation apparatus, the evaporated effluent is heated via the heating device to increase the temperature of the evaporated effluent. The distillate oil is collected in two or more batches with each of the batches being associated with different temperature ranges of the evaporated effluent. The evaporated effluent is heated to about 130° C. to about 150° C. and the first batch of distillate oil is collected. The first batch of distillate oil generally will include terpenes, heat-sensitive impurities, triglycerides, solvent residuals, and/or other undesired components.

The evaporated effluent is then heated to about 160° C. Once the temperature of the evaporated extract is stable for about 20 minutes, the temperature is increased slowly until about 180° C. Preferably, the temperature setting of the heating device is raised in 10° C. increments every 15 minutes until the evaporated extract is at about 180° C. The second batch of distillate oil is collected between about 160° C. and about 180° C. The second batch is collected when the evaporated effluent is about 160° C. and as the temperature of the evaporated effluent is being slowly increased. When only a second batch of distillate oil is collected from the evaporated effluent, that distillate oil may be referred to as the "final distillate oil" or "second pass distillate oil."

Preferably, a third batch of distillate oil is collected during the increase of temperature to about 180° C. One or more characteristics of the distillate oil may change during the temperature increase between about 160° C. and about 180° C. The third batch may be collected when there is change in the characteristic(s). In some embodiments, there is a change in tone and/or color in the distillate oil and the darker tone/darker color distillate oil (e.g., lighter color to redder) is preferably collected in the third batch. The second batch of distillate oil may have a higher purity of CBD and/or THC compounds compared to the third batch of distillate oil. When a third batch is collected, the second and third batches of distillate oil from step 118 are processed separately under steps 120-122. One or both of the second and third batches of distillate oil from step 118 may be referred to as "final distillate oil" or "second pass distillate oil."

One or more desired terpenes may be added to the final distillate oil at step 210. Preferably, the amount of terpenes added does not exceed 1 gram per 1 kilogram of the final distillate oil to provide for a little flavor but not an overwhelming amount of flavor.

Other embodiments of method 100 may include one or more additional steps. For example, when the final distillate oil will be used for inhalers, the final distillate oil may be mixed via an emulsifier at step 122. A rotor-stator homogenizer, such as the PRO250 Homogenizer from PRO Scientific, is a suitable emulsifier. Additionally, a medical grade propellant, such as R134 may be added prior to filling the inhaler cartridges with the emulsified distillate oil.

Although method 100 shows a particular sequence of steps, one or more embodiments of method 100 may include a different sequence of steps. Additionally, or alternatively, one or more steps of method 100 may be modified, added, replaced, and/or repeated. For example, steps 110-118 may be repeated once or twice prior to step 120 to produce a final distillate oil that is purer. Alternatively, or additionally, steps 118 and/or 122 may be omitted.

B. Selected Embodiments and Claim Concepts

This section describes additional aspects and features of methods of producing a CBD/THC oil, presented without limitation as a series of paragraphs, some or all of which may be alphanumerically designated for clarity and efficiency. Each of these paragraphs can be combined with one or more other paragraphs, and/or with disclosure from elsewhere in this application, in any suitable manner. Some of the paragraphs below may expressly refer to and further limit other paragraphs, providing without limitation examples of some of the suitable combinations.

A1. A method of producing a CBD/THC oil, comprising:
extracting CBD/THC from plant matter using one or more solvents;
winterizing the solvent extract;
evaporating the one or more solvents from the winterized extract;
distilling the evaporated extract via a short path distillation apparatus to produce an initial distillate oil;
mixing the initial distillate oil with at least one solvent;
running the mixture of initial distillate oil and at least one solvent through a chromatography column to produce an effluent;
evaporating the at least one solvent from the effluent;
distilling the evaporated effluent via a short path distillation apparatus to produce a final distillate oil; and
mixing one or more desired terpenes with the final distillate oil.

A2. The method of paragraph A1, wherein mixing the initial distillate oil with at least one solvent includes mixing the initial distillate oil with n-heptane.

A3. The method of any of paragraphs A1-A2, further comprising mixing the final distillate oil with an emulsifier.

A4. The method of any of paragraphs A1-A3, wherein running the mixture of initial distillate oil and at least one solvent includes running the mixture of initial distillate oil and at least one solvent through a chromatography column having a stationary bed with activated magnesium silicate.

A5. The method of any of paragraphs A1-A4, wherein extracting CBD/THC from plant matter using one or more solvents includes extracting CBD/THC from plant matter using a mixture of propane and n-butane.

A6. The method of paragraph A5, wherein extracting CBD/THC from plant matter using a mixture of propane and n-butane includes extracting CBD/THC from plant matter using a mixture of about 70% propane and about 30% n-butane.

A7. The method of any of paragraphs A1-A6, wherein extracting CBD/THC from plant matter using one or more solvents includes extracting CBD/THC from plant matter using ethanol at temperatures between about -40° C. and about -80° C.

A8. The method of paragraph A7, wherein extracting CBD/THC from plant matter using ethanol includes recirculating the ethanol through the plant matter.

A9. The method of any of paragraphs A1-A8, wherein winterizing the solvent extract includes:
adding solvent to the solvent extract to form a winterizing mixture;
chilling the winterizing mixture to a temperature between about -40° C. and about -80° C.; and
filtering the chilled winterizing mixture to remove solids.

A10. The method of paragraph A9, wherein filtering the solvent extract includes running the solvent extract through first, second, and third filters, the first filter having a first micron rating, the second filter having a second micron rating, and the third filter having a third micron rating, wherein the first micron rating is greater than the second micron rating, and the second micron rating is greater than the third micron rating.

A11. The method of paragraph A10, wherein the third micron rating is between about 1 micron and about 3 microns.

A12. The method of any of paragraphs A1-A11, wherein evaporating the one or more solvents from the winterized extract includes evaporating the one or more solvents from the winterized extract via a rotary evaporator.

A13. The method of any of paragraphs A1-A12, wherein evaporating the at least one solvent from the effluent includes evaporating the at least one solvent from the effluent via a rotary evaporator.

A14. The method of any of paragraphs A1-A13, wherein distilling the evaporated extract includes increasing the temperature of the evaporated extract to collect first, second, and third batches of initial distillate oil, each of the first, second, and third batches of initial distillate oil are associated with a different temperature range of the evaporated extract, wherein the initial distillate oil is from one of the second and third batches.

A15. The method of any of paragraphs A1-A14, wherein distilling the evaporated effluent includes increasing the temperature of the evaporated effluent to collect first, second, and third batches of final distillate oil, each of the first, second, and third batches of final distillate oil are associated with a different temperature range of the evaporated extract, wherein the final distillate oil is from one of the second and third batches.

Advantages, Features, Benefits

The different embodiments and examples of the methods of producing a CBD/THC oil described herein provide several advantages over known solutions for producing a CBD/THC oil. For example, illustrative embodiments and examples described herein produce a very pure distillate oil (e.g., 90% to ≥99%) that is suitable for dispensing via inhalers. The distillate oil produced has almost no wax.

No known method, system, or device can produce the above results. However, not all embodiments and examples described herein provide the same advantages or the same degree of advantage.

Conclusion

The disclosure set forth above may encompass multiple distinct examples with independent utility. Although each of these examples has been disclosed in its preferred form(s), the specific embodiments thereof as disclosed and illustrated herein are not to be considered in a limiting sense, because numerous variations are possible. The subject matter of the example(s) includes all novel and nonobvious combinations and subcombinations of the various elements, features, functions, and/or properties disclosed herein.

Certain combinations and subcombinations regarded as novel and nonobvious are particularly pointed out throughout this disclosure. Other combinations and subcombinations of features, functions, elements, and/or properties may be claimed, with or without variation in scope, in applications claiming priority from this or a related application.

Explicit reference is hereby made to all examples, embodiments, inventions, labels, terms, descriptions, and illustrative measurements shown in the drawings and/or in any included appendices, whether or not described further herein. To the extent that section headings are used within this disclosure, such headings are for organizational purposes only.

What is claimed is:

1. A method of producing at least one of a CBD or THC oil, comprising:
   extracting at least one of CBD or THC from plant matter using a mixture of propane and n-butane;
   winterizing the solvent extract;
   evaporating the mixture of propane and n-butane from the winterized extract via heating the winterized extract;
   distilling the extract from the evaporating the mixture of propane and n-butane step via a first short path distillation apparatus to produce an initial distillate oil;
   mixing the initial distillate oil with at least one solvent;
   running the mixture of initial distillate oil and at least one solvent through a chromatography column to produce an effluent;
   evaporating the at least one solvent from the effluent;
   distilling the effluent from the evaporating the at least one solvent step via a second short path distillation apparatus to produce a final distillate oil; and
   mixing one or more desired terpenes with the final distillate oil.

2. The method of claim 1, wherein mixing the initial distillate oil with at least one solvent includes mixing the initial distillate oil with n-heptane.

3. The method of claim 1, further comprising mixing the final distillate oil with an emulsifier.

4. The method of claim 1, wherein running the mixture of initial distillate oil and at least one solvent includes running the mixture of initial distillate oil and at least one solvent through a chromatography column having a stationary bed with activated magnesium silicate.

5. The method of claim 1, wherein the at least one solvent is at least one of pentane, hexane, and n-heptane.

6. The method of claim 1, wherein extracting at least one of CBD or THC from plant matter using a mixture of propane and n-butane includes extracting at least one of CBD or THC from plant matter using a mixture of about 70% propane and about 30% n-butane.

7. The method of claim 1, wherein the first short path distillation apparatus is the same as the second short path distillation apparatus.

8. The method of claim 1, wherein winterizing the solvent extract includes:
   adding a second solvent to the solvent extract to form a winterizing mixture;
   chilling the winterizing mixture to a temperature between about -40° C. and about -80° C.; and
   filtering the chilled winterizing mixture to remove solids.

9. The method of claim 8, wherein filtering the solvent extract includes running the solvent extract through first, second, and third filters, the first filter having a first micron rating, the second filter having a second micron rating, and the third filter having a third micron rating, wherein the first micron rating is greater than the second micron rating, and the second micron rating is greater than the third micron rating.

10. The method of claim 9, wherein the third micron rating is between about 1 micron and about 3 microns.

11. The method of claim 8, wherein the second solvent is the same as the at least one solvent.

12. The method of claim 1, wherein evaporating the mixture of propane and n-butane from the winterized extract includes evaporating the mixture of propane and n-butane from the winterized extract via a rotary evaporator.

13. The method of claim 1, wherein evaporating the at least one solvent from the effluent includes evaporating the at least one solvent from the effluent via a rotary evaporator.

14. The method of claim 1, wherein distilling the extract from the evaporating the mixture of propane and n-butane step includes increasing the temperature of the extract from the evaporating the mixture of propane and n-butane step to collect first, second, and third batches of initial distillate oil, each of the first, second, and third batches of initial distillate oil are associated with a different temperature range of the extract from the evaporating the mixture of propane and n-butane step, wherein the initial distillate oil is from at least one of the second and third batches.

15. The method of claim 1, wherein distilling the effluent from the evaporating the at least one solvent step includes increasing the temperature of the effluent from the evaporating the at least one solvent step to collect first, second, and third batches of final distillate oil, each of the first, second, and third batches of final distillate oil are associated with a different temperature range of the extract from the evaporating the mixture of propane and n-butane step, wherein the final distillate oil is from at least one of the second and third batches.

* * * * *